US011642030B2

(12) United States Patent
Miyachi

(10) Patent No.: US 11,642,030 B2
(45) Date of Patent: May 9, 2023

(54) PHOTOACOUSTIC IMAGE GENERATION APPARATUS FOR DETECTING A TIP PORTION OF AN INSERT

(71) Applicant: FUJIFILM Corporation, Tokyo (JP)

(72) Inventor: Yukiya Miyachi, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 129 days.

(21) Appl. No.: 16/573,594

(22) Filed: Sep. 17, 2019

(65) Prior Publication Data
US 2020/0008683 A1 Jan. 9, 2020

Related U.S. Application Data

(63) Continuation of application No. PCT/JP2018/008196, filed on Mar. 5, 2018.

(30) Foreign Application Priority Data

Mar. 29, 2017 (JP) .............................. JP2017-064580

(51) Int. Cl.
*A61B 5/00* (2006.01)
(52) U.S. Cl.
CPC ............ *A61B 5/0095* (2013.01); *A61B 5/743* (2013.01)
(58) Field of Classification Search
CPC ..... A61B 5/0095; A61B 5/743; A61B 5/0084; A61B 5/06; A61B 8/13
See application file for complete search history.

(56) References Cited

U.S. PATENT DOCUMENTS 10,238,299 B2* 3/2019 Murakoshi ........... A61B 8/4416
10,492,693 B2* 12/2019 Irisawa .................. A61B 5/685
(Continued)

FOREIGN PATENT DOCUMENTS

JP 2015-43969 A 3/2015
JP 2015173922 A * 10/2015
(Continued)

OTHER PUBLICATIONS

International Preliminary Report on Patentability and Written Opinion of the International Searching Authority, dated Oct. 10, 2019, for International Application No. PCT/JP2018/008196, with an English Translation.

(Continued)

*Primary Examiner* — Boniface Ngathi N
*Assistant Examiner* — Zainab Mohammed Aldarraji
(74) *Attorney, Agent, or Firm* — Birch, Stewart, Kolasch & Birch, LLP

(57) ABSTRACT

An insert having a photoacoustic wave generation portion, an acoustic wave detection unit that detects photoacoustic waves and reflected acoustic waves, a photoacoustic image generation unit that generates a photoacoustic image on the basis of the photoacoustic waves, an image output unit that outputs information on the basis of the photoacoustic waves detected by the acoustic wave detection unit, a tip position detection unit that detects that a tip portion of the insert is disposed at a predetermined detection position with respect to the acoustic wave detection unit, and a control unit that displays information on the basis of intensity of a detection signal of the photoacoustic waves generated from the photoacoustic wave generation portion on image display as an insert inspection mode in a case where it is detected that the tip portion of the insert is disposed at the predetermined detection position are included.

20 Claims, 8 Drawing Sheets

(56) References Cited

U.S. PATENT DOCUMENTS

| | | | |
|---|---|---|---|
| 10,758,129 B2* | 9/2020 | Irisawa | A61B 8/4254 |
| 10,786,159 B2* | 9/2020 | Irisawa | A61B 8/4416 |
| 11,006,837 B2* | 5/2021 | Miyachi | A61B 8/461 |
| 2013/0096430 A1* | 4/2013 | Yoshiara | A61B 8/463 |
| | | | 600/438 |
| 2014/0142507 A1* | 5/2014 | Armes | A61M 5/20 |
| | | | 604/112 |
| 2015/0297092 A1* | 10/2015 | Irisawa | A61B 17/3403 |
| | | | 600/407 |
| 2016/0135689 A1* | 5/2016 | Murakoshi | A61B 5/0095 |
| | | | 600/407 |
| 2016/0183841 A1* | 6/2016 | Duindam | A61M 25/01 |
| | | | 600/424 |
| 2017/0071475 A1* | 3/2017 | Irisawa | A61B 1/07 |
| 2019/0307421 A1* | 10/2019 | Yamamoto | A61B 8/15 |
| 2021/0045715 A1* | 2/2021 | Mauldin | A61N 7/00 |

FOREIGN PATENT DOCUMENTS

| | | |
|---|---|---|
| JP | 2015-231583 A | 12/2015 |
| JP | 2016-36673 A | 3/2016 |
| JP | 2016036673 A * | 3/2016 |
| WO | WO 2017/169188 A1 | 10/2017 |

OTHER PUBLICATIONS

International Search Report, dated May 29, 2018, for International Application No. PCT/JP2018/008196, with an English translation.

* cited by examiner

PHOTOACOUSTIC IMAGE GENERATION APPARATUS FOR DETECTING A TIP PORTION OF AN INSERT

CROSS-REFERENCE TO RELATED APPLICATIONS

This application is a Continuation of PCT International Application No. PCT/JP2018/008196 filed on Mar. 5, 2018, which claims priority under 35 U.S.C § 119(a) to Japanese Patent Application No. 2017-064580 filed on Mar. 29 2017. Each of the above application(s) is hereby expressly incorporated by reference, in its entirety, into the present application.

BACKGROUND OF THE INVENTION

1. Field of the Invention

The present invention relates to a photoacoustic image generation apparatus comprising an insert of which at least a portion is inserted into a subject and which includes a photoacoustic wave generation portion that absorbs light and generates photoacoustic waves.

2. Description of the Related Art

An ultrasonography method has been known as a kind of image inspection method that can non-invasively inspect the internal state of a living body. In ultrasonography, an ultrasound probe that can transmit and receive ultrasonic waves is used. In a case in which the ultrasound probe transmits ultrasonic waves to a subject (living body), the ultrasonic waves travel in the living body and are reflected from the interface between tissues. The ultrasound probe receives the reflected ultrasonic waves and a distance is calculated on the basis of the time until the reflected ultrasonic waves return to the ultrasound probe. In this way, it is possible to capture an image indicating the internal aspect of the living body.

In addition, photoacoustic imaging has been known which captures the image of the inside of a living body using a photoacoustic effect. In general, in the photoacoustic imaging, the inside of the living body is irradiated with pulsed laser light. In the inside of the living body, a living body tissue absorbs the energy of the pulsed laser light and ultrasonic waves (photoacoustic waves) are generated by adiabatic expansion caused by the energy. For example, an ultrasound probe detects the photoacoustic waves and a photoacoustic image is formed on the basis of a detection signal. In this way, it is possible to visualize the inside of the living body on the basis of the photoacoustic waves.

In addition, as a technique related to the photoacoustic imaging, JP2015-231583A discloses a puncture needle in which a photoacoustic wave generation portion that absorbs light and generates photoacoustic waves is provided in the vicinity of a tip. In the puncture needle, an optical fiber is provided up to the tip of the puncture needle and laser light emitted from a laser light source is guided by the optical fiber to be emitted to the photoacoustic wave generation portion. An ultrasound probe detects the photoacoustic waves generated by the photoacoustic wave generation portion and a photoacoustic image is generated on the basis of a detection signal of the photoacoustic waves. In the photoacoustic image, a part of the photoacoustic wave generation portion appears as a bright point, which makes it possible to check the position of the puncture needle using the photoacoustic image.

SUMMARY OF THE INVENTION

In the photoacoustic imaging using the puncture needle generating the photoacoustic waves from the vicinity of the tip as described in JP2015-231583A, in a case where the laser light with a predetermined output is not emitted due to deterioration or failure of the laser light source, in a case where the laser light is not successfully guided to the photoacoustic wave generation portion due to breakage, damage, or contamination of the optical fiber, in a case where there is a trouble such as peeling in the photoacoustic wave generation portion, decrease in photoacoustic wave generation efficiency, or the like, and the like, there is a problem that the photoacoustic waves with a normal output are not generated from the vicinity of the puncture needle tip and thus it is impossible to generate an accurate photoacoustic image.

JP2016-036673A discloses a correction process in a photoacoustic image generation apparatus. Here, the correction process is performed on the basis of the photoacoustic waves generated in a structural reference body by emitting light from the outside to the structural reference body for photoacoustic imaging. However, in this method, it is impossible to check whether an output of photoacoustic waves generated by a puncture needle itself is normal, which is regarded as the problem in the above.

The invention has been made in view of the above-mentioned problems and an object of the invention is to provide a photoacoustic image generation apparatus capable of detecting whether an output of photoacoustic waves from the vicinity of a tip of an insert is normal in the photoacoustic image generation apparatus using the insert that generates the photoacoustic waves from the vicinity of the tip.

A photoacoustic image generation apparatus according to the invention comprises: an insert of which at least a tip portion is inserted into a subject and which includes a light guide member that guides light to the tip portion and a photoacoustic wave generation portion that absorbs the light guided by the light guide member and generates photoacoustic waves; an acoustic wave detection unit that detects the photoacoustic waves emitted from the photoacoustic wave generation portion; a photoacoustic image generation unit that generates a photoacoustic image on the basis of the photoacoustic waves detected by the acoustic wave detection unit; an image output unit that outputs information on the basis of the photoacoustic waves detected by the acoustic wave detection unit to image display; a tip position detection unit that detects that the tip portion of the insert is disposed at a predetermined detection position with respect to the acoustic wave detection unit; and a control unit that displays information on the basis of intensity of a detection signal of the photoacoustic waves generated from the photoacoustic wave generation portion on the image display as an insert inspection mode in a case where the tip position detection unit detects that the tip portion of the insert is disposed at the predetermined detection position.

In the photoacoustic image generation apparatus according to the invention, the control unit may display a detection region corresponding to the predetermined detection position on the photoacoustic image.

In the photoacoustic image generation apparatus according to the invention, the acoustic wave detection unit may further detect reflected acoustic waves reflected by transmission of acoustic waves to the subject. The photoacoustic image generation apparatus may further comprise an acoustic image generation unit that generates an acoustic image on the basis of the reflected acoustic waves detected by the acoustic wave detection unit. The control unit may display a detection region corresponding to the predetermined detection position on the acoustic image.

In the photoacoustic image generation apparatus according to the invention, it is preferable that the predetermined detection position is relatively changeable with respect to the acoustic wave detection unit.

In this case, it is preferable that the control unit changes reference intensity in a case where intensity of a signal indicating the insert is determined, on the basis of a relative position of the predetermined detection position with respect to the acoustic wave detection unit.

In the photoacoustic image generation apparatus according to the invention, it is preferable that the control unit performs display instructing a direction in the case where the tip portion of the insert is disposed at the predetermined detection position.

In the photoacoustic image generation apparatus according to the invention, it is preferable that the control unit warns a user on the basis of signal intensity of the photoacoustic waves indicating the insert in the insert inspection mode.

In the photoacoustic image generation apparatus according to the invention, the control unit may display a measurement result on the basis of signal intensity of the photoacoustic waves indicating the insert in the insert inspection mode and a display map having recorded thereon a relationship between the signal intensity of the photoacoustic waves and display contents.

In the photoacoustic image generation apparatus according to the invention, the control unit may display a state of signal intensity of the photoacoustic waves indicating the insert in the insert inspection mode by a character and/or a graph.

In the photoacoustic image generation apparatus according to the invention, the acoustic wave detection unit may comprise a detection element array in which a plurality of detection elements that detect the photoacoustic waves are arranged, and the control unit may use only reception signals of some of the detection elements corresponding to the predetermined detection position in the insert inspection mode for generation of a measurement result.

In the photoacoustic image generation apparatus according to the invention, the acoustic wave detection unit may comprise a detection element array in which a plurality of detection elements that detect the photoacoustic waves are arranged, and the control unit may use only reception signals of some of the detection elements that detect a signal exceeding predetermined signal intensity in the insert inspection mode for generation of a measurement result.

In the photoacoustic image generation apparatus according to the invention, it is preferable that the control unit displays only a point with an amplitude equal to or larger than a predetermined ratio with respect to a maximum amplitude in the same frame on the photoacoustic image.

In this case, it is preferable that the control unit displays the point with the amplitude equal to or larger than the predetermined ratio with respect to the maximum amplitude by one color on the basis of signal intensity.

In the photoacoustic image generation apparatus according to the invention, it is preferable that the control unit performs correction such that intensity of a detected reception signal is equal to signal intensity which is the reference on the basis of a detection result in the insert inspection mode.

It is preferable that the insert is a needle that is inserted into the subject.

In the photoacoustic image generation apparatus according to the invention, the photoacoustic image generation apparatus using the insert that generates the photoacoustic waves from the vicinity of the tip detects that the tip portion of the insert is disposed at the predetermined detection position with respect to the acoustic wave detection unit and displays information on the basis of intensity of a detection signal of the photoacoustic waves generated from the photoacoustic wave generation portion as an insert inspection mode. Therefore, it is possible to detect whether an output of the photoacoustic waves from the vicinity of the tip of the insert is normal.

DESCRIPTION OF THE PREFERRED EMBODIMENTS

Figure 1:
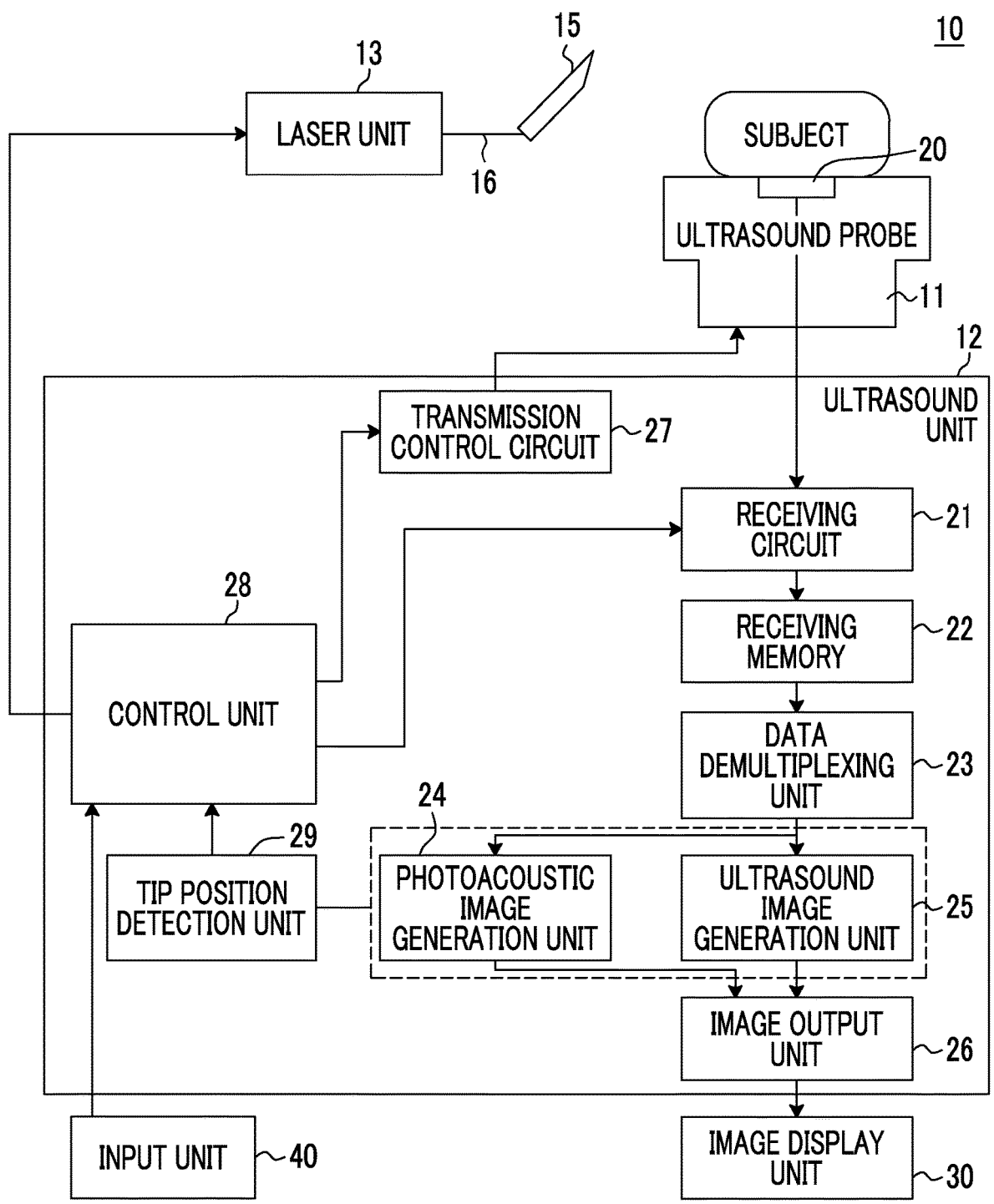
FIG. 1 is a block diagram schematically illustrating the configuration of a first embodiment of a photoacoustic image generation apparatus according to the invention.

Hereinafter, a first embodiment of a photoacoustic image generation apparatus according to the invention will be described in detail with reference to the drawings. FIG. 1 is a block diagram schematically illustrating the configuration of the first embodiment of the photoacoustic image generation apparatus according to the invention.

As illustrated in FIG. 1, a photoacoustic image generation apparatus 10 according to this embodiment comprises an ultrasound probe 11, an ultrasound unit 12, a laser unit 13, and a puncture needle 15. The puncture needle 15 and the laser unit 13 are connected by an optical cable 16 having an optical fiber. The puncture needle 15 can be attached to and detached from the optical cable 16 and is disposable. In addition, in this embodiment, ultrasonic waves are used as acoustic waves. However, the invention is not limited to the ultrasonic waves. Acoustic waves with an audible frequency may be used as long as an appropriate frequency can be selected according to, for example, an inspection target or measurement conditions.

The laser unit 13 comprises a solid-state laser light source using, for example, yttrium aluminum garnet (YAG) and alexandrite. Laser light emitted from the solid-state laser light source of the laser unit 13 is guided by the optical cable 16 and is incident on the puncture needle 15. The laser unit 13 according to this embodiment emits pulsed laser light in a near-infrared wavelength range. The near-infrared wavelength range means a wavelength range approximately from 700 nm to 850 nm. In this embodiment, the solid-state laser light source is used. However, other laser light sources, such as a gas laser light source, may be used or light sources other than the laser light source may be used.

Figure 2:
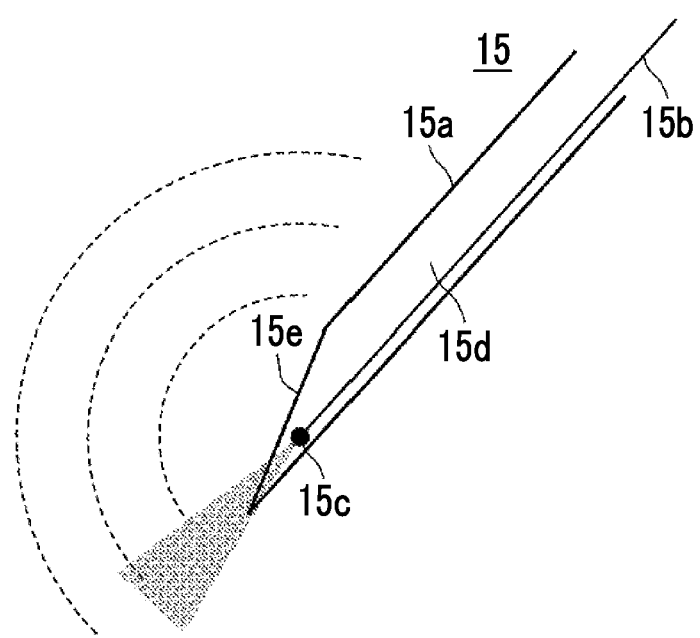
FIG. 2 is a cross-sectional view of the configuration of a tip portion of a puncture needle.

The puncture needle 15 is an embodiment of an insert according to the invention and is a needle that is inserted into a subject. FIG. 2 is a cross-sectional view including a center axis that extends in a length direction of the puncture needle 15. The puncture needle 15 includes a puncture needle main body 15a that has an opening on an acute tip surface 15e and is formed in a hollow shape, an optical fiber 15b (corresponding to a light guide member according to the invention) that guides laser light emitted from the laser unit 13 to the vicinity of the opening of the puncture needle 15, and a photoacoustic wave generation portion 15c that absorbs laser light emitted from the optical fiber 15b and generates photoacoustic waves.

The optical fiber 15b and the photoacoustic wave generation portion 15c are disposed in a hollow portion 15d of the puncture needle main body 15a. For example, the optical fiber 15b is connected to the optical fiber in the optical cable 16 (see FIG. 1) through an optical connector that is provided at the base end of the puncture needle 15. For example, laser light of 0.2 mJ is emitted from a light emission end of the optical fiber 15b.

The photoacoustic wave generation portion 15c is provided at the light emission end of the optical fiber 15b and is provided in the vicinity of the tip of the puncture needle 15 and in the inner wall of the puncture needle main body 15a. The photoacoustic wave generation portion 15c absorbs the laser light emitted from the optical fiber 15b and generates photoacoustic waves. The photoacoustic wave generation portion 15c is made of, for example, an epoxy resin, a polyurethane resin, a fluorine resin, and silicone rubber with which a black pigment is mixed. In FIG. 2, the photoacoustic wave generation portion 15c is illustrated to be larger than the optical fiber 15b. However, the invention is not limited thereto. The photoacoustic wave generation portion 15c may have a size that is equal to the diameter of the optical fiber 15b.

The photoacoustic wave generation portion 15c is not limited to the above, and a metal film or an oxide film having light absorptivity with respect to the wavelength of laser light may be used as the photoacoustic wave generation portion. An oxide film made of, for example, iron oxide, chromium oxide, or manganese oxide having high light absorptivity with respect to the wavelength of laser light can be used as the photoacoustic wave generation portion 15c. Alternatively, a metal film made of, for example, titanium (Ti) or platinum (Pt) that has lower light absorptivity than an oxide and has higher biocompatibility than an oxide may be used as the photoacoustic wave generation portion 15c. In addition, the position where the photoacoustic wave generation portion 15c is provided is not limited to the inner wall of the puncture needle main body 15a. For example, a metal film or an oxide film which is the photoacoustic wave generation portion 15c may be formed on the light emission end of the optical fiber 15b with a thickness of about 100 nm by vapor deposition such that the oxide film covers the light emission end. In this case, at least a portion of the laser light emitted from the light emission end of the optical fiber 15b is absorbed by the metal film or the oxide film covering the light emission end and photoacoustic waves are generated from the metal film or the oxide film.

Returning to FIG. 1, the ultrasound probe 11 detects the photoacoustic waves emitted from the photoacoustic wave generation portion 15c after the puncture needle 15 is inserted into the subject. The ultrasound probe 11 comprises an acoustic wave detection unit that detects the photoacoustic waves.

The acoustic wave detection unit comprises a piezoelectric element array 20 in which a plurality of piezoelectric elements that detect the photoacoustic waves are one-dimensionally arranged and a multiplexer (not illustrated). The piezoelectric element is an ultrasound transducer, and the ultrasound transducer is a piezoelectric element made of a polymer film such as piezoelectric ceramics or polyvinylidene fluoride (PVDF). The acoustic wave detection unit comprises an acoustic lens, an acoustic matching layer, a backing member, a control circuit of the piezoelectric element array, and the like (not illustrated).

With the piezoelectric element array 20 of the acoustic wave detection unit, the ultrasound probe 11 transmits the acoustic waves (ultrasonic waves) to the subject and receives the reflected acoustic waves (reflected ultrasonic waves) with respect to the transmitted ultrasonic waves, in addition to the detection of the photoacoustic waves. In addition, the transmission and reception of the ultrasonic waves may be performed at different positions. For example, ultrasonic waves may be transmitted from a position different from the ultrasound probe 11, and the piezoelectric element array 20 of the ultrasound probe 11 may receive the reflected ultrasonic waves with respect to the transmitted ultrasonic waves. For example, a linear ultrasound probe, a convex ultrasound probe, or a sector ultrasound probe may be used as the ultrasound probe 11.

The ultrasound unit 12 includes the receiving circuit 21, a receiving memory 22, a data demultiplexing unit 23, a photoacoustic image generation unit 24, an ultrasound image generation unit 25, an image output unit 26, a transmission control circuit 27, a control unit 28, and a tip position detection unit 29. The ultrasound unit 12 typically includes, for example, a processor, a memory, and a bus. In the ultrasound unit 12, a program related to, for example, a photoacoustic image generation process, an ultrasound image generation process, and a process of detecting that a tip portion of the puncture needle 15 is disposed at a predetermined detection position with respect to the ultrasound probe 11 is incorporated into a memory. The program is operated by the control unit 28 which is formed by a processor to implement the functions of the data demultiplexing unit 23, the photoacoustic image generation unit 24, the ultrasound image generation unit 25, the image output unit 26, and the tip position detection unit 29. That is, each of these units is formed by the memory into which the program has been incorporated and the processor.

The hardware configuration of the ultrasound unit 12 is not particularly limited and can be implemented by combining, for example, a plurality of integrated circuits (ICs), a processor, an application specific integrated circuit (ASIC), a field-programmable gate array (FPGA), and a memory as appropriate.

The receiving circuit 21 receives a detection signal output from the ultrasound probe 11 and stores the received detection signal in the receiving memory 22. The receiving circuit 21 typically includes a low-noise amplifier, a variable-gain amplifier, a low-pass filter, and an analog-to-digital convertor (AD convertor). The detection signal of the ultrasound probe 11 is amplified by the low-noise amplifier, is subjected to gain adjustment corresponding to a depth by the variable-gain amplifier, is converted into a digital signal by the AD convertor after a high-frequency component of the detection signal is cut by the low-pass filter, and then is stored in the receiving memory 22. The receiving circuit 21 is formed by, for example, one integrated circuit (IC).

The ultrasound probe 11 outputs a detection signal of the photoacoustic waves and a detection signal of the reflected ultrasonic waves. The receiving memory 22 stores the AD-converted detection signals (sampling data) of the photoacoustic waves and the reflected ultrasonic waves. The data demultiplexing unit 23 reads the detection signal of the photoacoustic waves from the receiving memory 22 and transmits the detection signal to the photoacoustic image generation unit 24. The data demultiplexing unit 23 reads the detection signal of the reflected ultrasonic waves from the receiving memory 22 and transmits the detection signal to the ultrasound image generation unit 25.

The photoacoustic image generation unit 24 generates a photoacoustic image on the basis of the detection signal of the photoacoustic waves detected by the ultrasound probe 11. The photoacoustic image generation process includes, for example, image reconfiguration such as phasing addition, detection, and logarithmic conversion. The ultrasound image generation unit 25 generates an ultrasound image (corresponding to an acoustic image according to the invention) that displays the internal state of the living body of the subject using a two-dimensional image on the basis of the detection signal of the reflected ultrasonic waves detected by the ultrasound probe 11. The ultrasound image generation process includes image reconfiguration, such as phasing addition, detection, and logarithmic conversion. The image output unit 26 outputs the photoacoustic image and the ultrasound image on an image display unit 30 such as a display apparatus.

The control unit 28 controls each component in the ultrasound unit 12. For example, in a case in which a photoacoustic image is acquired, the control unit 28 transmits a trigger signal to the laser unit 13 such that the laser unit 13 emits laser light. In addition, the control unit 28 transmits a sampling trigger signal to the receiving circuit 21 to control, for example, the sampling start time of the photoacoustic waves with the emission of the laser light. Sampling data received by the receiving circuit 21 is stored in the receiving memory 22.

The photoacoustic image generation unit 24 receives the sampling data of the detection signal of the photoacoustic waves through the data demultiplexing unit 23 and performs detection at a predetermined detection frequency to generate the photoacoustic image. The photoacoustic image generated by the photoacoustic image generation unit 24 is input to the image output unit 26.

In a case in which an ultrasound image is acquired, the control unit 28 transmits an ultrasound transmission trigger signal for commanding the transmission of ultrasonic waves to the transmission control circuit 27. In a case in which the ultrasound transmission trigger signal is received, the transmission control circuit 27 causes the ultrasound probe 11 to transmit ultrasonic waves. In a case in which the ultrasound image is acquired, the ultrasound probe 11 performs a scanning, for example, while shifting a reception region of a group of piezoelectric elements line by line to detect the reflected ultrasonic waves by the control of the control unit 28. The control unit 28 transmits the sampling trigger signal to the receiving circuit 21 according to the transmission time of ultrasonic waves to start the sampling of the reflected ultrasonic waves. Sampling data received by the receiving circuit 21 is stored in the receiving memory 22.

The ultrasound image generation unit 25 receives the sampling data of the detection signal of the photoacoustic waves through the data demultiplexing unit 23 and performs the detection at a predetermined detection frequency to generate the ultrasound image. The ultrasound image generated by the ultrasound image generation unit 25 is input to the image output unit 26.

The tip position detection unit 29 detects a position of the tip portion of the puncture needle 15 on the basis of the photoacoustic image generated by the photoacoustic image generation unit 24 or the ultrasound image generated by the ultrasound image generation unit 25.

In a case of detecting the tip position of the puncture needle 15 on the basis of the photoacoustic image, for example, a position of the maximum brightness point in the photoacoustic image may be detected as the position of the tip portion of the puncture needle 15. In practice, there is a case where a light artifact and a sound artifact may occur and a photoacoustic image is generated as if the photoacoustic waves are detected from a plurality of positions. Therefore, there is a case where the original position of the tip portion of the puncture needle 15 cannot be specified.

For this reason, the photoacoustic image generated by the photoacoustic image generation unit 24 is not used as it is, but, for example, a smoothing treatment may be performed for the photoacoustic image to prevent erroneous detection caused by the artifacts. Specifically, the smoothing treatment is performed for the photoacoustic image subjected to detection and logarithmic conversion. For example, a filtering process using a Gaussian filter can be used as the smoothing treatment. It is preferable that the size of the Gaussian filter is less than that of the tip portion of the puncture needle 15.

Then, the photoacoustic image after the smoothing treatment is subjected to a binarization process to generate a binary image. Then, a region in which white pixels are continuously distributed is detected from the binary image to detect the position of the tip portion of the puncture needle 15. In this way, it is possible to detect the position of the tip portion of the puncture needle 15 with higher accuracy.

In a case of detecting the tip position of the puncture needle 15 on the basis of the ultrasound image, there is a case where the position of the tip portion of the puncture needle 15 cannot be specified accurately in a case where determination is made by a position of the maximum brightness point in the entire image since other pieces of stuff such as a living cell and a blood vessel often appear in addition to the puncture needle 15.

For this reason, in a case where a depth range where the puncture needle 15 is assumed to be disposed is set in advance, a profile is measured for each line with the same depth in the depth range in the ultrasound image, and the maximum value in the profile exceeds a predetermined threshold value, determination may be made that the puncture needle 15 is detected at the position.

In the profile, in a case where an average value, standard deviation, and the maximum value are obtained, a condition equation such as the following equation is defined, and determination is made that the puncture needle 15 is detected in a case where the condition equation is satisfied, it is possible to further enhance detection accuracy.

$$\text{Maximum Value} > \text{Average Value} + \text{Standard Deviation} \times 3$$

The detection method of the position of the tip portion of the puncture needle 15 on the basis of the photoacoustic image or the ultrasound image described above is merely an example, and the invention is not limited thereto. The detection may be performed by any method.

Figure 3:
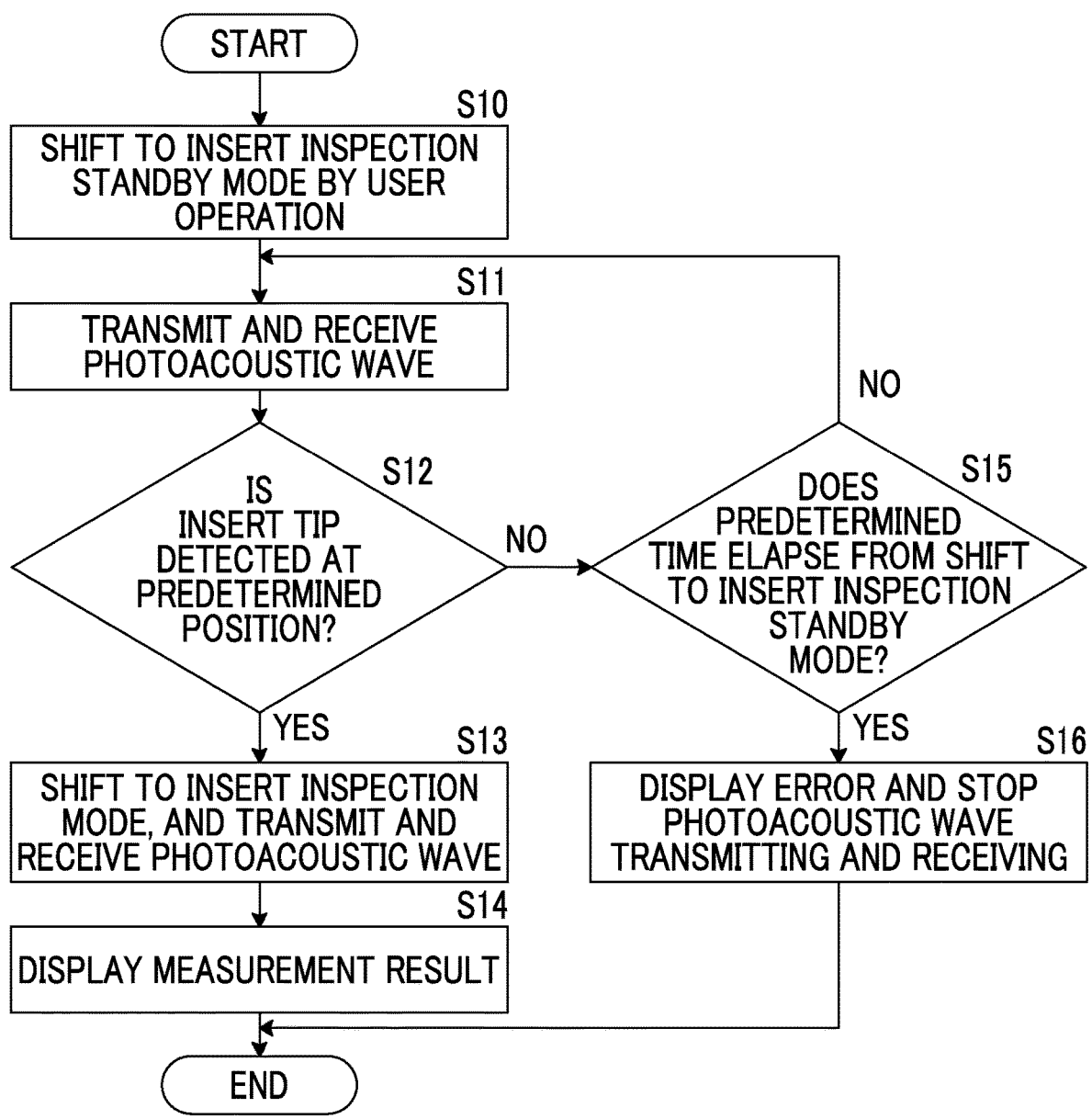
FIG. 3 is a flowchart for describing an inspection method of the puncture needle in the photoacoustic image generation apparatus according to the first embodiment.

Here, an inspection method of the puncture needle 15 by the control unit 28 will be described in detail. FIG. 3 is a flowchart for describing the inspection method of the puncture needle in the photoacoustic image generation apparatus according to this embodiment.

In a case where a user operation is received and a mode shifts to a puncture needle (insert) inspection standby mode (S10), the control unit 28 starts photoacoustic wave transmitting and receiving (S11) and determines whether the tip portion of the puncture needle 15 is detected at the predetermined detection position with respect to the ultrasound probe (acoustic wave detection unit) 11 (S12).

Here, an instruction from the user to shift to the puncture needle (insert) inspection standby mode is input to the control unit 28 through an input unit 40. For an interface in this case, in a case where an icon for shifting to the puncture needle (insert) inspection standby mode is displayed on the image display unit 30 and, for example, the icon is clicked by a mouse connected as the input unit 40, the mode may be shifted to the puncture needle (insert) inspection standby mode. Alternatively, a dedicated physical button for shifting to the puncture needle (insert) inspection standby mode may be provided in the photoacoustic image generation apparatus.

Figure 4:
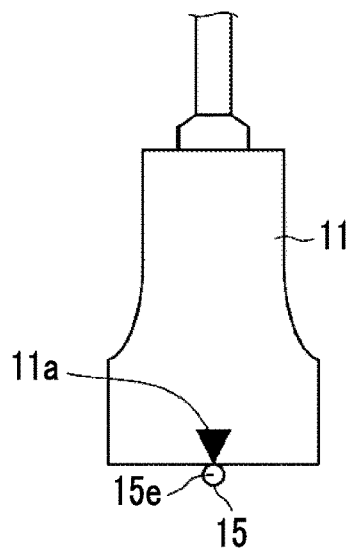
FIG. 4 is a front view of an example of an ultrasound probe.
Figure 5:
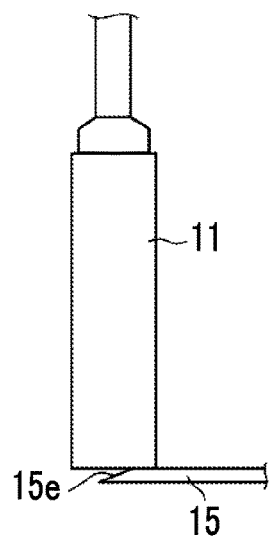
FIG. 5 is a side surface view of the ultrasound probe illustrated in FIG. 4.
Figure 6:
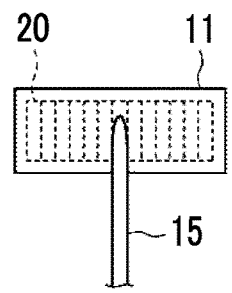
FIG. 6 is a lower surface view of the ultrasound probe illustrated in FIG. 4.
Figure 7:
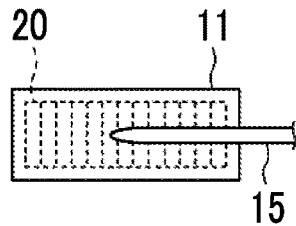
FIG. 7 is the lower surface view of the ultrasound probe illustrated in FIG. 4.
Figure 8:
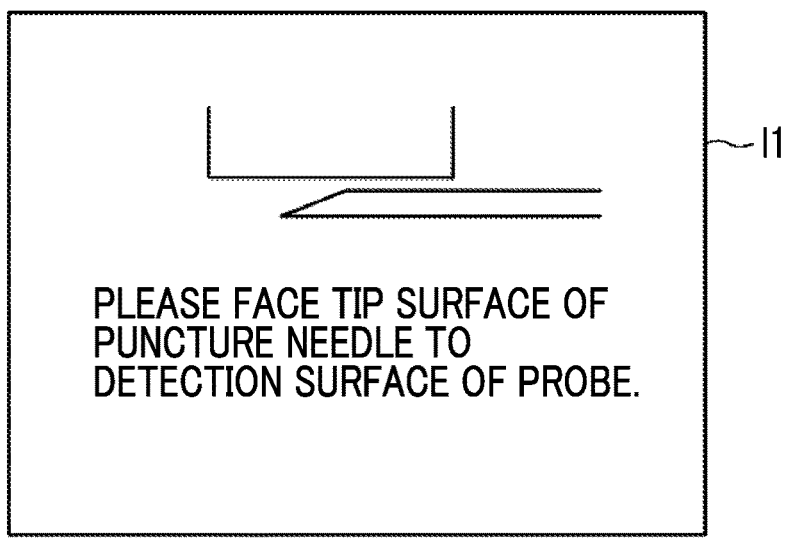
FIG. 8 is a diagram illustrating an example of a display screen of a puncture needle installation instruction.
Figure 9:
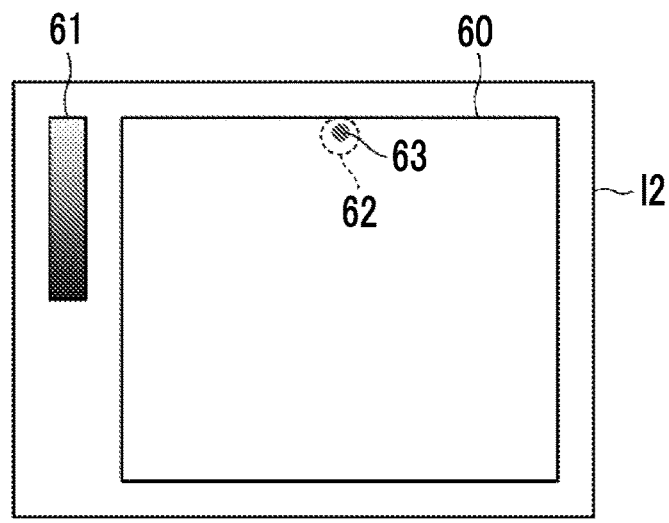
FIG. 9 is a diagram illustrating an example of a display screen at the time of the puncture needle inspection.

The predetermined detection position with respect to the ultrasound probe (acoustic wave detection unit) 11 is set in advance and will be described in detail using drawings herein. FIG. 4 is a front view of an example of the ultrasound probe. FIG. 5 is a side surface view of the ultrasound probe illustrated. FIGS. 6 and 7 are lower surface views of the ultrasound probe illustrated. FIG. 8 is a diagram illustrating an example of a display screen of a puncture needle installation instruction. FIG. 9 is a diagram illustrating an example of a display screen at the time of the puncture needle inspection.

In a case where the puncture needle 15 is inspected, it is preferable that the puncture needle 15 is set in the vicinity of the center of a detection surface (lower surface) of the ultrasound probe 11, as illustrated in FIGS. 4 to 6, since it is possible to receive a signal with high intensity in a case where the ultrasound probe 11 and the puncture needle 15 are brought as close as possible. In this case, in a case where a piezoelectric element arrangement direction of the piezoelectric element array 20 and a longitudinal direction of the puncture needle 15 are in parallel to each other as illustrated in FIG. 7, there may be an artifact at the time of the inspection. Therefore, it is preferable that the piezoelectric element arrangement direction of the piezoelectric element array 20 and the longitudinal direction of the puncture needle 15 are orthogonal to each other as illustrated in FIG. 6. A standard display 11a such as an arrow which is a standard of the installation position at the time of the inspection of the puncture needle 15 may be provided on a surface of the ultrasound probe 11.

Even in a case where the photoacoustic waves with the same intensity are generated from the puncture needle 15, reception signal intensity in the ultrasound probe 11 changes in a case where the orientation of the tip surface 15e of the puncture needle 15 with respect to the detection surface of the ultrasound probe 11 changes. A state where the tip surface 15e of the puncture needle 15 faces a detection surface side of the ultrasound probe 11 is the best reception state. Therefore, in the case where the puncture needle 15 is inspected, it is necessary to make the state where the tip surface 15e of the puncture needle 15 faces the detection surface side of the ultrasound probe 11, as illustrated in FIGS. 4 to 6, each time.

For this purpose, in the case where the mode shifts to the inspection standby mode, as in a display screen I1 illustrated in FIG. 8, an instruction by a sentence such as "Please face the tip surface of the puncture needle to the detection surface of the probe (ultrasound probe 11)" may be displayed on the image display unit 30 together with a picture indicating an installation form such that the user makes the state where the tip surface 15e of the puncture needle 15 faces the detection surface side of the ultrasound probe 11.

As in a display screen I2 illustrated in FIG. 9, a photoacoustic image 60 generated on the basis of the transmitting and receiving of the photoacoustic waves in the puncture needle (insert) inspection standby mode may be displayed in real time and a detection region 62 corresponding to the predetermined detection position may be displayed on the photoacoustic image 60 as an aid in the case where the user installs the puncture needle 15 at the predetermined detection position.

In a case where the tip portion of the puncture needle 15 is detected at the predetermined detection position with respect to the ultrasound probe (acoustic wave detection unit) 11 in step S12, the mode shifts to a puncture needle (insert) inspection mode to start the photoacoustic wave transmitting and receiving (S13), a measurement result is displayed (S14), and the process ends.

Here, the measurement in step S13 is performed a plurality of frames (for example, about five frames) and the measurement result is obtained on the basis of an average value of the measurements. In this way, it is possible to improve the accuracy of the measurement.

Figure 10:
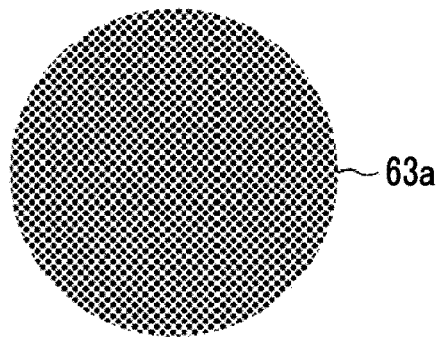
FIG. 10 is a diagram illustrating a display example of the puncture needle in the display screen.
Figure 11:
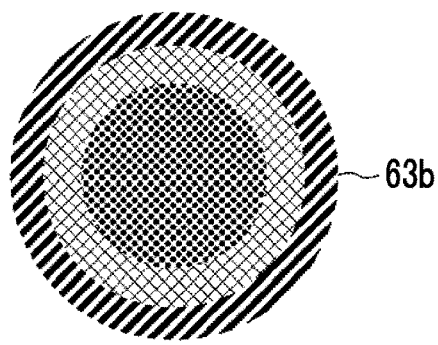
FIG. 11 is a diagram illustrating a display example of the puncture needle in the display screen.
Figure 12:
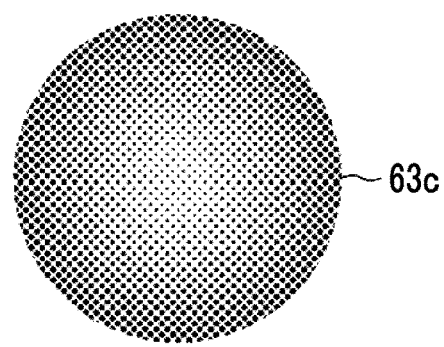
FIG. 12 is a diagram illustrating a display example of the puncture needle in the display screen.
Figure 13:
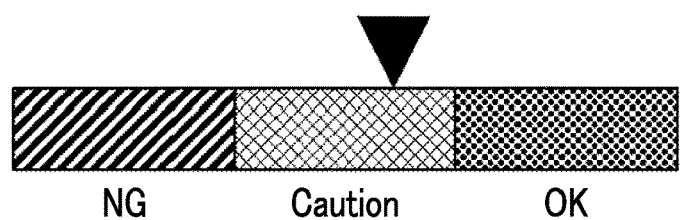
FIG. 13 is a diagram illustrating a display example of an inspection result of the puncture needle.

The display of measurement result will be described in detail using drawings. FIGS. 10 to 12 are diagrams illustrating display examples of the puncture needle in the display screen. FIG. 13 is a diagram illustrating a display example of an inspection result of the puncture needle.

In the puncture needle (insert) inspection mode, since it is already known that the tip portion of the puncture needle 15 is at the predetermined detection position with respect to the ultrasound probe 11, only reception signals of some piezoelectric elements (some piezoelectric elements close to the puncture needle 15) corresponding to the predetermined detection position or only reception signals of some piezoelectric elements that detect a signal exceeding a predetermined signal intensity are used for the generation of the measurement result. In this way, it is possible to reduce the noise at the time of the detection.

As in the display screen I2 illustrated in FIG. 9, the measurement result is displayed by changing a display color of a bright point 63 indicating the position of the tip portion of the puncture needle 15 on the photoacoustic image 60 on the basis of a display map 61 indicating a relationship between the signal intensity of the photoacoustic waves and the display color.

The display color in the display map 61 is set such that it can be recognized whether the signal intensity from the tip portion of the puncture needle 15 is normal, abnormal, or in the middle thereof compared with a predetermined appropriate reference intensity. For example, the display color can be blue at a normal time, green in a case where the signal intensity decreases 15% from the maximum amplitude at the normal time, and red in a case where the signal intensity decreases 30% from the maximum amplitude at the normal time. The signal intensity at the normal time may be a reception amplitude in a case where, for example, the photoacoustic waves of about $1.0 \times 10^{-7}$ $mJ/cm^2$ are received from a needle tip.

Here, it is preferable that the bright point 63 indicating the measurement result is displayed in a single color as a bright point 63a illustrated in FIG. 10. However, the signal intensity is low in the periphery of the bright point 63 compared with the center thereof. Therefore, in a case where the signal intensity is directly replaced with the display color of the display map 61 and is displayed for each pixel indicating the bright point 63, the display color is changed in a ring shape in one bright point as a bright point 63b illustrated in FIG. 11. In this way, it is difficult for the user to accurately grasp the measurement result.

For this reason, it is preferable that an image in which only points with an amplitude equal to or larger than a predetermined ratio with respect to the maximum amplitude in the same frame on the photoacoustic image are displayed, which is displayed in one representative color on the basis of the signal intensity obtained by averaging these points, or in which hue is decided at the maximum value of the signal intensity and the brightness is displayed in gradation by the decided one representative color is displayed as a bright point 63c illustrated in FIG. 12. Here, the fact that only the points with the amplitude equal to or larger than the predetermined ratio with respect to the maximum amplitude in the same frame are used for the display means that the noise with the same level as the order of the maximum amplitude is reduced to some extent, and the predetermined ratio may be set according to the noise level as appropriate. For example, only points with an amplitude of 10% or more with respect to the maximum amplitude may be used for the display in a case where the noise is relatively small, and only points with an amplitude of 70% or more with respect to the maximum amplitude may be used for the display in a case where the noise is relatively large.

For the display of the measurement result, the invention is not limited to the display by the display color of the bright point 63 on the photoacoustic image 60 as described above. The display may be performed by a character such as a word such as "normal, caution, abnormal" or "OK, Caution, NG", an actual measurement value (unit $mJ/cm^2$, $mW/cm^2$, or the like) of the signal intensity from the tip portion of the puncture needle 15, or a numerical value (for example, 95%, Level 8, or the like) in a case where the signal intensity from the tip portion of the puncture needle 15 is compared with a normal value. In addition, the display may be performed on the basis of a graph as illustrated in FIG. 13. Furthermore, the display may be performed by combining these.

Furthermore, in a case where the signal intensity from the tip portion of the puncture needle 15 is different compared with the predetermined appropriate reference intensity, calibration (correction) may be performed such that the signal intensity from the tip portion of the puncture needle 15 becomes equal to the predetermined appropriate reference intensity. This calibration may be automatically performed by the photoacoustic image generation apparatus after step S14 or may be performed on the basis of the instruction from the user.

The instruction from the user is input to the control unit 28 through the input unit 40. For the interface in this case, in a case where an icon for performing the calibration is displayed on the image display unit 30 and, for example, the icon is clicked by a mouse connected as the input unit 40, the calibration may be performed. Alternatively, a dedicated physical button for performing the calibration may be provided in the photoacoustic image generation apparatus.

For the calibration operation, a reception gain of the receiving circuit 21 may be corrected such that the signal intensity from the tip portion of the puncture needle 15 becomes equal (for example, within ±20% of the appropriate reference intensity) to the predetermined appropriate reference intensity.

An output variation of the laser light in the laser unit 13 is often a factor that the signal intensity from the tip portion of the puncture needle 15 changes. Therefore, in a case where a correction amount of the reception gain for each individual of the laser unit 13 connected to the ultrasound unit 12 is held and an individual laser unit 13 already acquiring the correction amount of the reception gain is connected, the calibration may be automatically performed on the basis of the held correction amount of the reception gain without performing the inspection of the puncture needle 15.

For the calibration operation, the invention is not limited to the correction of the reception gain of the receiving circuit 21 as described above, and an operation condition (input voltage or pulse length at the time of light source driving) of the laser unit 13 may be adjusted.

It is possible to extend the lifetime of the laser unit 13 and the puncture needle 15 by performing such a calibration operation.

In a case where the tip portion of the puncture needle 15 is not detected at the predetermined detection position with respect to the ultrasound probe (acoustic wave detection unit) 11 in step S12, it is determined whether a predetermined time elapses from the shift to the puncture needle (insert) inspection standby mode (S15). In a case where the predetermined time does not elapse, the process returns to step S11. In a case where the predetermined time elapses, an error is displayed, the photoacoustic wave transmitting and receiving is stopped (S16), and the process ends.

Specifically, in a case where the tip portion of the puncture needle 15 is not detected for about 10 seconds, for example, an error display such as "The ultrasonic waves equal to or larger than a predetermined output are not detected from the needle tip. Please check whether the needle tip is in contact with the probe (ultrasound probe 11) surface. In a case where the needle tip is in contact with the probe (ultrasound probe 11) surface, it may be in failure." is performed. Accordingly, even in a case where the laser light guided by the optical fiber 15b leaks to the outside due to, for example, peeling of the photoacoustic wave generation portion 15c in the vicinity of the tip of the puncture needle 15, it is possible to improve the safety since the irradiation of the laser light is stopped for a predetermined time without continuing the leak of the laser light.

As described above, since the photoacoustic image generation apparatus 10 according to the embodiment performs the inspection on the basis of the output of the photoacoustic waves generated by the puncture needle 15 itself, it is possible to surely detect the trouble of the laser unit 13 and the puncture needle 15. Since the photoacoustic image generation apparatus 10 according to the embodiment can be adapted to a common photoacoustic image generation apparatus, new hardware for the inspection is unnecessary. Since the detection is automatically performed by detecting that the tip portion of the puncture needle 15 is disposed at the predetermined detection position, it is unnecessary for the user to check whether an installation state of the puncture needle 15 is correct and thus it is possible to improve the convenience.

Figure 14:
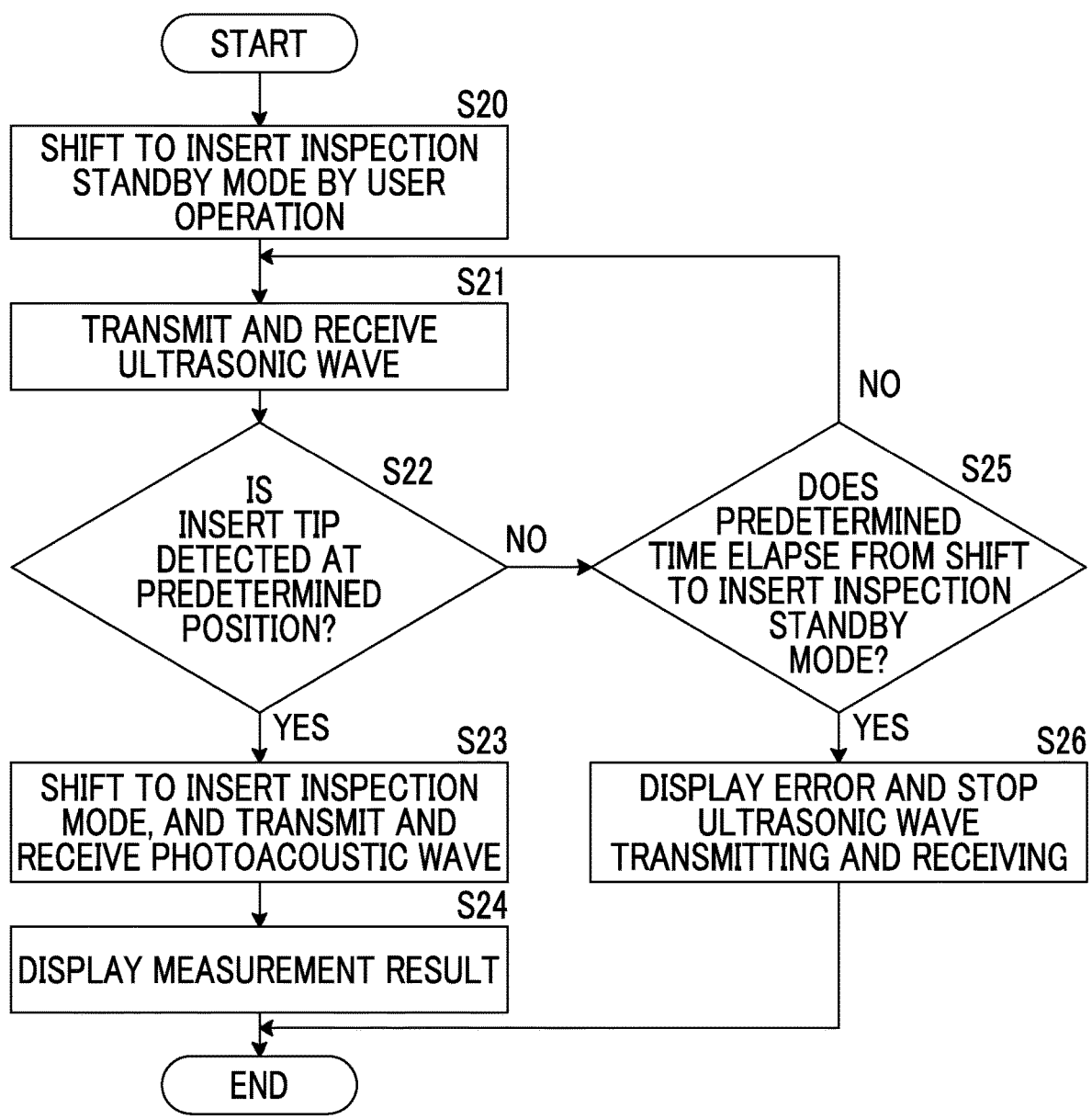
FIG. 14 is a flowchart for describing another inspection method of the puncture needle in the photoacoustic image generation apparatus according to the first embodiment.

In the embodiment, the photoacoustic wave transmitting and receiving is performed to detect the tip portion of the puncture needle 15 with the photoacoustic image at the time of the shift to the puncture needle (insert) inspection standby mode. However, the ultrasound transmitting and receiving may be performed to detect the tip portion of the puncture needle 15 with the ultrasound image at the time of the shift to the puncture needle (insert) inspection standby mode as in a flowchart illustrated in FIG. 14.

Figure 15:
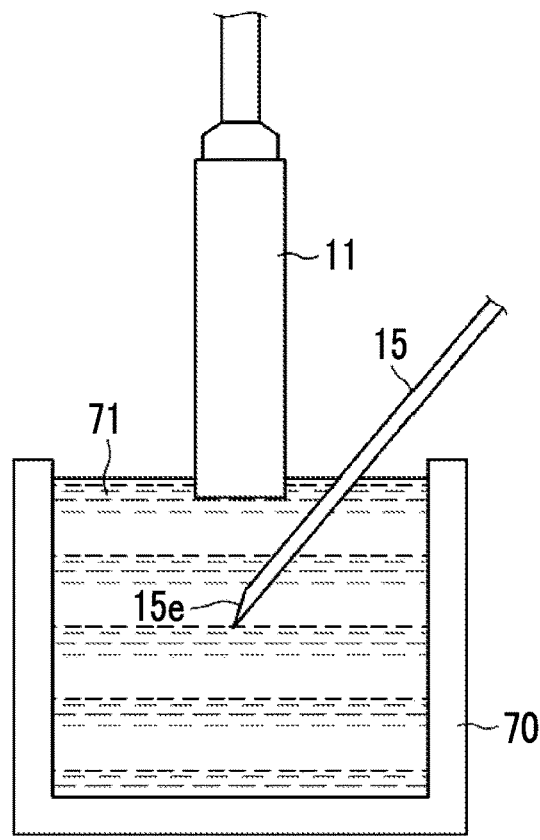
FIG. 15 is a diagram illustrating an installation form of the puncture needle at the time of the puncture needle inspection in a photoacoustic image generation apparatus according to a second embodiment.
Figure 16:
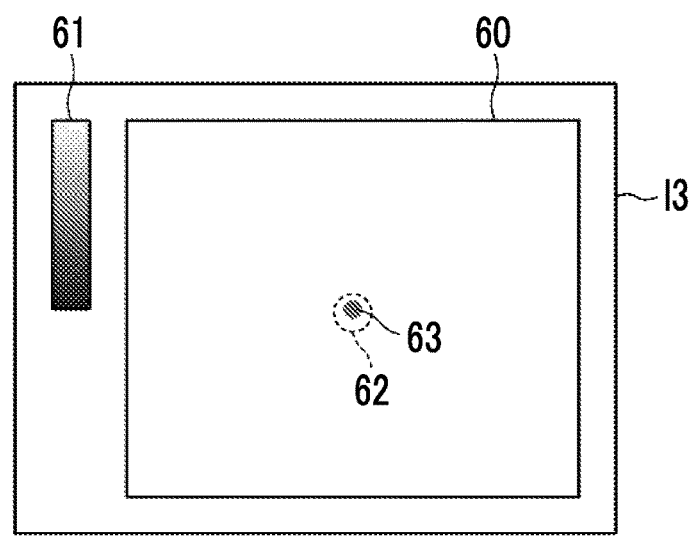
FIG. 16 is a diagram illustrating an example of a display screen at the time of the puncture needle inspection.

Next, a second embodiment of the photoacoustic image generation apparatus according to the invention will be described. In the photoacoustic image generation apparatus 10 according to the first embodiment, the predetermined detection position with respect to the ultrasound probe (acoustic wave detection unit) 11 is set in the vicinity of the center of the detection surface (lower surface) of the ultrasound probe 11. However, in this embodiment, it is assumed that the puncture needle 15 is installed in a water tank or the like. FIG. 15 is a diagram illustrating an installation form of the puncture needle at the time of the puncture needle inspection in the photoacoustic image generation apparatus according to the second embodiment. FIG. 16 is a diagram illustrating an example of a display screen at the time of the puncture needle inspection.

In the embodiment, it is assumed that the puncture needle 15 is inserted into water 71 stored in a water tank 70 at the time of the shift to the puncture needle (insert) inspection standby mode. In this case, the predetermined detection position with respect to the ultrasound probe (acoustic wave detection unit) 11 is a position separated from the center of the detection surface (lower surface) of the ultrasound probe 11 as illustrated in FIG. 15. This predetermined detection position can be adjusted by the user, and, for example, the user may move the position of detection region 62 displayed on the photoacoustic image 60 up and down through the input unit 40 to perform the adjustment as in a display screen 13 illustrated in FIG. 16.

In this case, the reception signal intensity decreases as the tip portion of the puncture needle 15 separates from the detection surface of the ultrasound probe 11. Therefore, it is necessary to adjust also the appropriate reference intensity at the time of determining a state of the signal intensity from the tip portion of the puncture needle 15 on the basis of a distance from the detection surface of the ultrasound probe 11 to the predetermined detection position and an ultrasound attenuation rate of a medium around the puncture needle 15.

For example, in a case where the medium around the puncture needle 15 is the water 71, the frequency of the photoacoustic waves generated in the puncture needle 15 is 5 MHz, and the distance from the detection surface of the ultrasound probe 11 to the predetermined detection position is 1 cm, it is necessary to set the appropriate reference intensity to −0.01 (dB) as follows. The appropriate reference intensity is −0 (dB) in a case where the distance from the detection surface of the ultrasound probe 11 to the predetermined detection position is 0 cm, the intensity is −0.02 (dB) in a case where the distance is 2 cm, and the intensity is −0.05 (dB) in a case where the distance is 5 cm.

0.002 (dB/(MHz·cm))×5 (MHz)×1 (cm)=0.01 (dB)

A phantom may be used instead of the water tank 70 as described above. The ultrasound attenuation rate of the phantom is about 0.5 (dB/(MHz·cm)).

Also with such a form, it is possible to obtain the same effect as the first embodiment described above.

In the above-described first and second embodiments, the puncture needle 15 is used as an embodiment of the insert. However, the invention is not limited thereto as the insert. The insert may be a radio-frequency ablation needle including an electrode that is used for radio-frequency ablation therein, a catheter that is inserted into a blood vessel, or a guide wire for a catheter that is inserted into a blood vessel. Alternatively, the insert may be an optical fiber for laser treatment.

The insert is not limited to a needle, such as an injection needle, and may be a biopsy needle used for biopsy. That is, the needle may be a biopsy needle that is inserted into an inspection target of the living body and extracts the tissues of a biopsy site of the inspection target. In this case, photoacoustic waves may be generated from an extraction portion (intake port) for sucking and extracting the tissues of the biopsy site. In addition, the needle may be used as a guiding needle that is used for insertion into a deep part, such as a part under the skin or an organ inside the abdomen.

The invention has been described above on the basis of the preferred embodiments. However, the photoacoustic image generation apparatuses according to the invention are not limited only to the above-described embodiments. Various modifications and changes of the configurations according to the above-described embodiments are also included in the scope of the invention.

EXPLANATION OF REFERENCES

10: photoacoustic image generation apparatus
11: ultrasound probe
12: ultrasound unit
13: laser unit
15: puncture needle
15a: puncture needle main body
15b: optical fiber
15c: photoacoustic wave generation portion
15d: hollow portion
15e: tip surface
16: optical cable
20: acoustic wave detection unit
21: receiving circuit
22: receiving memory
23: data demultiplexing unit
24: photoacoustic image generation unit
25: ultrasound image generation unit
26: image output unit
27: transmission control circuit
28: control unit
29: tip position detection unit
30: image display unit
40: input unit
60: photoacoustic image/ultrasound image
61: display map
62: detection region
63, 63a, 63b, 63c: bright point
70: water tank
71: water I1 to I3: display screen

What is claimed is:

1. A photoacoustic image generation apparatus comprising:
- an insert of which at least a tip portion is configured to be inserted into a subject and which includes a light guide member that guides light to the tip portion and a photoacoustic wave generation portion that absorbs the light guided by the light guide member and generates photoacoustic waves;
- an acoustic wave detection unit which comprises a detection array in which a plurality of detection elements that detect the photoacoustic waves emitted from the photoacoustic wave generation portion are arranged;
- a processor configured to generate a photoacoustic image on the basis of the photoacoustic waves detected;
- an image display configured to display the photoacoustic image; and
- a memory configured to store a first photoacoustic wave detection region located outside the subject and corresponding to a predetermined photoacoustic wave detection position set on a detection surface of the acoustic wave detection unit in advance;
- wherein the processor is further configured to:
  - shift to an insert inspection standby mode based on a user operation via an input unit, irradiate the photoacoustic wave generation portion with a light, detect the photoacoustic wave generated from the photoacoustic generation portion, and determine whether the tip portion of the insert is detected at the first photoacoustic wave detection region;
  - shift to an insert inspection mode in a case where the tip portion of the insert is detected at the first photoacoustic wave detection region, irradiate the photoacoustic wave generation portion with a light, and measure intensity of a detected signal of the photoacoustic wave generated from the photoacoustic generation portion; and
  - display measurement result on the basis of intensity of a detection signal of the photoacoustic waves generated from the photoacoustic wave generation portion on the image display.

2. The photoacoustic image generation apparatus according to claim 1,
wherein the processor is further configured to display a detection region corresponding to the first photoacoustic wave detection region on the photoacoustic image.

3. The photoacoustic image generation apparatus according to claim 1,
wherein the acoustic wave detection unit is further configured to detect reflected acoustic waves reflected by transmission of acoustic waves to the subject,
wherein the processor is further configured to generate an acoustic image on the basis of the reflected acoustic waves detected and
display a detection region corresponding to the first photoacoustic wave detection region on the acoustic image.

4. The photoacoustic image generation apparatus according to claim 1,
wherein the first photoacoustic wave detection region is changeable with respect to the acoustic wave detection unit.

5. The photoacoustic image generation apparatus according to claim 2,
wherein the first photoacoustic wave detection region is changeable with respect to the acoustic wave detection unit.

6. The photoacoustic image generation apparatus according to claim 3,
wherein the first photoacoustic wave detection region is changeable with respect to the acoustic wave detection unit.

7. The photoacoustic image generation apparatus according to claim 4,
wherein the processor is further configured to change a reference intensity in order to compare to the intensity of a detection signal of the photoacoustic waves generated from the photoacoustic wave generation portion, on the basis of a relative position of the first photoacoustic wave detection region with respect to the acoustic wave detection unit.

8. The photoacoustic image generation apparatus according to claim 5,
wherein the processor is further configured to change a reference intensity in order to compare to the intensity of a detection signal of the photoacoustic waves generated from the photoacoustic wave generation portion on the basis of a relative position of the first photoacoustic wave detection region with respect to the acoustic wave detection unit.

9. The photoacoustic image generation apparatus according to claim 6,
wherein the processor is further configured to change a reference intensity in order to compare to the intensity of the detection signal of the photoacoustic waves generated from the photoacoustic wave generation portion, on the basis of a relative position of the first detection region with respect to the acoustic wave photoacoustic wave detection unit.

10. The photoacoustic image generation apparatus according to claim 1,
wherein the processor is further configured to display an instruction instructing a direction in the case when the tip portion of the insert is disposed at the first photoacoustic wave detection region.

11. The photoacoustic image generation apparatus according to claim 2,
wherein the processor is further configured to display an instruction instructing a direction in the case when the tip portion of the insert is disposed at the first photoacoustic wave detection region.

12. The photoacoustic image generation apparatus according to claim 1,
wherein the processor is further configured to warn a user on the basis of signal intensity of the photoacoustic waves indicating the insert in the insert inspection mode.

13. The photoacoustic image generation apparatus according to claim 1,
wherein the processor is further configured to display the measurement result on the basis of the intensity of the detection signal of the photoacoustic waves generated from the photoacoustic wave generation portion in the insert inspection mode and a display map having recorded thereon a relationship between the intensity of the detection signal and display contents.

14. The photoacoustic image generation apparatus according to claim 1,
wherein the processor is further configured to display a state of the intensity of the detection signal of the photoacoustic waves generated from the photoacoustic wave generation portion in the insert inspection mode by a character and/or a graph.

15. The photoacoustic image generation apparatus according to claim 1,
wherein the processor is further configured to use only reception signals of some of the detection elements corresponding to the first photoacoustic wave detection region in the insert inspection mode for generation of the measurement result.

16. The photoacoustic image generation apparatus according to claim 1,
wherein the processor is further configured to use only reception signals of some of the detection elements that detect a signal exceeding predetermined signal intensity in the insert inspection mode for generation of the measurement result.

17. The photoacoustic image generation apparatus according to claim 1,
wherein the processor is further configured to display only a point with an amplitude equal to or larger than a predetermined ratio with respect to a maximum amplitude in the same frame on the photoacoustic image.

18. The photoacoustic image generation apparatus according to claim 17,
wherein the processor is further configured to display the point with the amplitude equal to or larger than the predetermined ratio with respect to the maximum amplitude by one color on the basis of the intensity of the detection signal of the photoacoustic waves generated from the photoacoustic wave generation portion.

19. The photoacoustic image generation apparatus according to claim 7,
wherein the processor is further configured to perform correction such that the intensity of the detection signal of the photoacoustic waves generated from the photoacoustic wave generation portion is equal to the reference intensity on the basis of a detection result in the insert inspection mode.

20. The photoacoustic image generation apparatus according to claim 1,
wherein the insert is a needle that is configured to be inserted into the subject.

* * * * *